US012691301B2

(12) United States Patent
Sugeno et al.

(10) Patent No.: US 12,691,301 B2
(45) Date of Patent: Jul. 28, 2026

(54) TREATMENT PLANNING APPARATUS, RADIATION TREATMENT APPARATUS, AND TREATMENT PLANNING METHOD

(71) Applicant: Canon Kabushiki Kaisha, Tokyo (JP)

(72) Inventors: Jinichi Sugeno, Nasushiobara (JP); Masanori Koyama, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 167 days.

(21) Appl. No.: 18/431,013

(22) Filed: Feb. 2, 2024

(65) Prior Publication Data

US 2024/0261595 A1 Aug. 8, 2024

(30) Foreign Application Priority Data

Feb. 3, 2023 (JP) ................................. 2023-015021

(51) Int. Cl.
*A61N 5/10* (2006.01)
(52) U.S. Cl.
CPC .................................. *A61N 5/1031* (2013.01)

(58) Field of Classification Search
None
See application file for complete search history.

(56) References Cited

U.S. PATENT DOCUMENTS

| | | | |
|---|---|---|---|
| 9,061,143 B2 | 6/2015 | Sasai et al. | |
| 2014/0252227 A1 | 9/2014 | Sasai et al. | |
| 2018/0369611 A1* | 12/2018 | Owens | A61N 5/1049 |

FOREIGN PATENT DOCUMENTS

WO WO 2013/054788 A1 4/2013

* cited by examiner

*Primary Examiner* — Hoon K Song
(74) *Attorney, Agent, or Firm* — Oblon, McClelland, Maier & Neustadt, L.L.P.

(57) ABSTRACT

A treatment planning apparatus according to an embodiment includes processing circuitry. The processing circuitry is configured to extract a tumor region rendered in a medical image. The processing circuitry is configured to extract a low oxygen region in the tumor region. The processing circuitry is configured to make a treatment plan for the tumor region, while using the low oxygen region as an index.

7 Claims, 8 Drawing Sheets

HTV REGION

HTV REGION

TUMOR REGION

HTV REGION

TREATMENT PLANNING APPARATUS, RADIATION TREATMENT APPARATUS, AND TREATMENT PLANNING METHOD

CROSS-REFERENCE TO RELATED APPLICATIONS

This application is based upon and claims the benefit of priority from Japanese Patent Application No. 2023-015021, filed on Feb. 3, 2023; the entire contents of which are incorporated herein by reference.

FIELD

Embodiments described herein relate generally to a treatment planning apparatus, a radiation treatment apparatus, and a treatment planning method.

BACKGROUND

Generally speaking, it is known that tissues in a low oxygen state have radiation resistance. In radiation treatment, differences in radiation resistance levels are taken into consideration among different tissues, but not taken into consideration among different regions in a tissue. In other words, treatment plans are not made to address the situation where the low oxygen states are different among the different regions in a tissue.

For example, for radiation treatment on a tissue that is in a low oxygen state and has radiation resistance, known methods include a method by which radiation is additionally applied (a boost irradiation) or radiation is applied after increasing sensitivity to radiation by using a sensitizer. In addition, in recent years, a phenomenon (called "the bystander effect") is drawing attention in which, when only a partial region of a tumor is irradiated with radiation, effects of the treatment are exerted as far as on tumor cells in the surroundings.

DETAILED DESCRIPTION

A treatment planning apparatus according to an embodiment includes processing circuitry. The processing circuitry is configured to extract a tumor region rendered in a medical image. The processing circuitry is configured to extract a low oxygen region in the tumor region. The processing circuitry is configured to make a treatment plan for the tumor region, while using the low oxygen region as an index.

Exemplary embodiments of a treatment planning apparatus, a radiation treatment apparatus, and a treatment planning method of the present disclosure will be explained in detail below, with reference to the accompanying drawings. The treatment planning apparatus, the radiation treatment apparatus, and the treatment planning method of the present disclosure are not limited by the embodiments described below. Further, it is possible to combine any of the embodiments with another embodiment or a conventional technique as long as no conflict occurs in the processing.

First Embodiment

Figure 1:
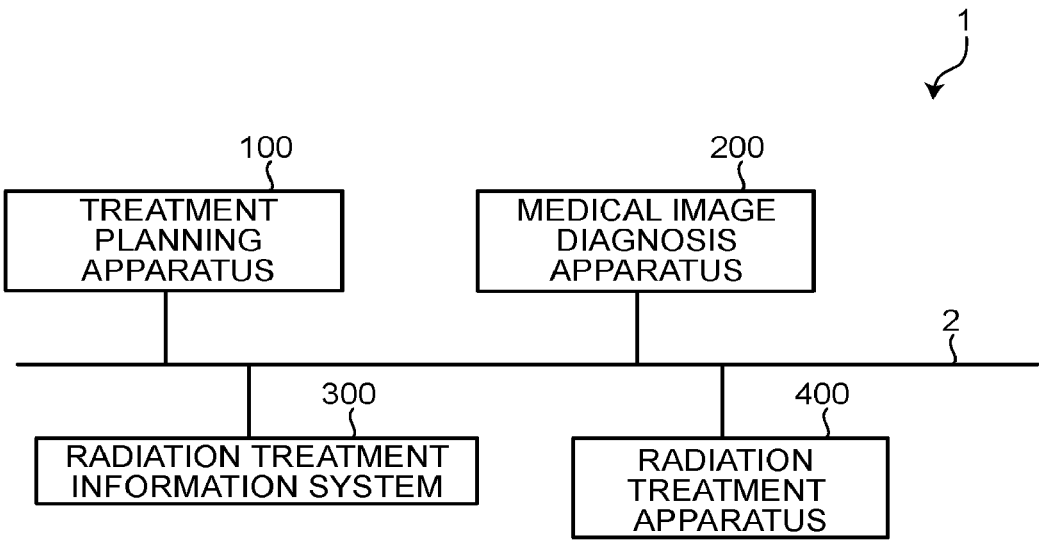
FIG. 1 is a diagram illustrating an exemplary configuration of a radiation treatment system according to a first embodiment.

To begin with, a radiation treatment system including a radiation treatment apparatus according to an embodiment of the present disclosure will be explained. FIG. 1 is a diagram illustrating an exemplary configuration of a radiation treatment system 1 according to a first embodiment. As illustrated in FIG. 1, the radiation treatment system 1 according to the first embodiment includes a treatment planning apparatus 100, a medical image diagnosis apparatus 200, a radiation treatment information system 300, and a radiation treatment apparatus 400. The treatment planning apparatus 100, the medical image diagnosis apparatus 200, the radiation treatment information system 300, and the radiation treatment apparatus 400 are connected so as to be able to communicate with one another via a network 2. Further, the configuration illustrated in FIG. 1 is merely an example, and possible embodiments are not limited to this example. For instance, the radiation treatment system 1 may include other various types of apparatuses and systems.

By using a three-dimensional medical image of a treated subject acquired by the medical image diagnosis apparatus 200, the treatment planning apparatus 100 is configured to make a treatment plan of radiation treatment to be carried out by the radiation treatment apparatus 400. More specifically, the treatment planning apparatus 100 is configured to make the treatment plan including irradiation parameters such as an irradiation angle of the radiation to be emitted by the radiation treatment apparatus 400 onto a treatment target site of which the position was specified by using the three-dimensional medical image, a dose and the shape of an irradiated field with respect to each irradiation angle, and the number of times of the irradiation. Further, the treatment planning apparatus 100 is configured to transmit the treatment plan to the radiation treatment information system 300 and to the radiation treatment apparatus 400. In this situation, the treatment planning apparatus 100 is configured to make the radiation treatment plan making use of the bystander effect. This configuration will be explained in detail later.

The medical image diagnosis apparatus 200 is configured to acquire the three-dimensional medical image to be used in the radiation treatment. Examples of the medical image diagnosis apparatus 200 include a Computed Tomography (CT) apparatus, a Magnetic Resonance Imaging (MRI) apparatus, a Positron Emission Tomography (PET) apparatus, an X-ray diagnosis apparatus and an ultrasound diagnosis apparatus capable of outputting three-dimensional images, and the like. The medical image diagnosis apparatus 200 being any of those listed above is configured to acquire the three-dimensional medical image rendering the treatment target site (e.g., a tumor) of the treated subject lying on a tabletop or a couchtop and to transmit the acquired three-dimensional medical image to the treatment planning apparatus 100.

The radiation treatment information system 300 is configured to record and manage various types of information related to the radiation treatment. More specifically, the radiation treatment information system 300 is configured to record and manage, with respect to each treated subject, various types of information related to progress of treatment such as a treatment plan, history information (an irradiation history), various types of reports, and records of statuses of the treated subject. The radiation treatment information system 300 can be accessed from any of the apparatuses connected to the network 2 and is able to provide the information managed therein.

The radiation treatment apparatus 400 is configured to carry out the radiation treatment by irradiating the treated subject with the radiation, according to the treatment plan made by the treatment planning apparatus 100. More specifically, the radiation treatment apparatus 400 is configured to carry out the radiation treatment on the treated subject, by obtaining the treatment plan from the treatment planning apparatus 100 via the radiation treatment information system 300 and emitting the radiation according to the irradiation parameter included in the obtained treatment plan. In this situation, the radiation treatment apparatus 400 according to the present embodiment may emit the radiation being any of the following: an electron beam, an X-ray, a gamma ray, a proton beam, and a heavy ion beam.

Figure 2:
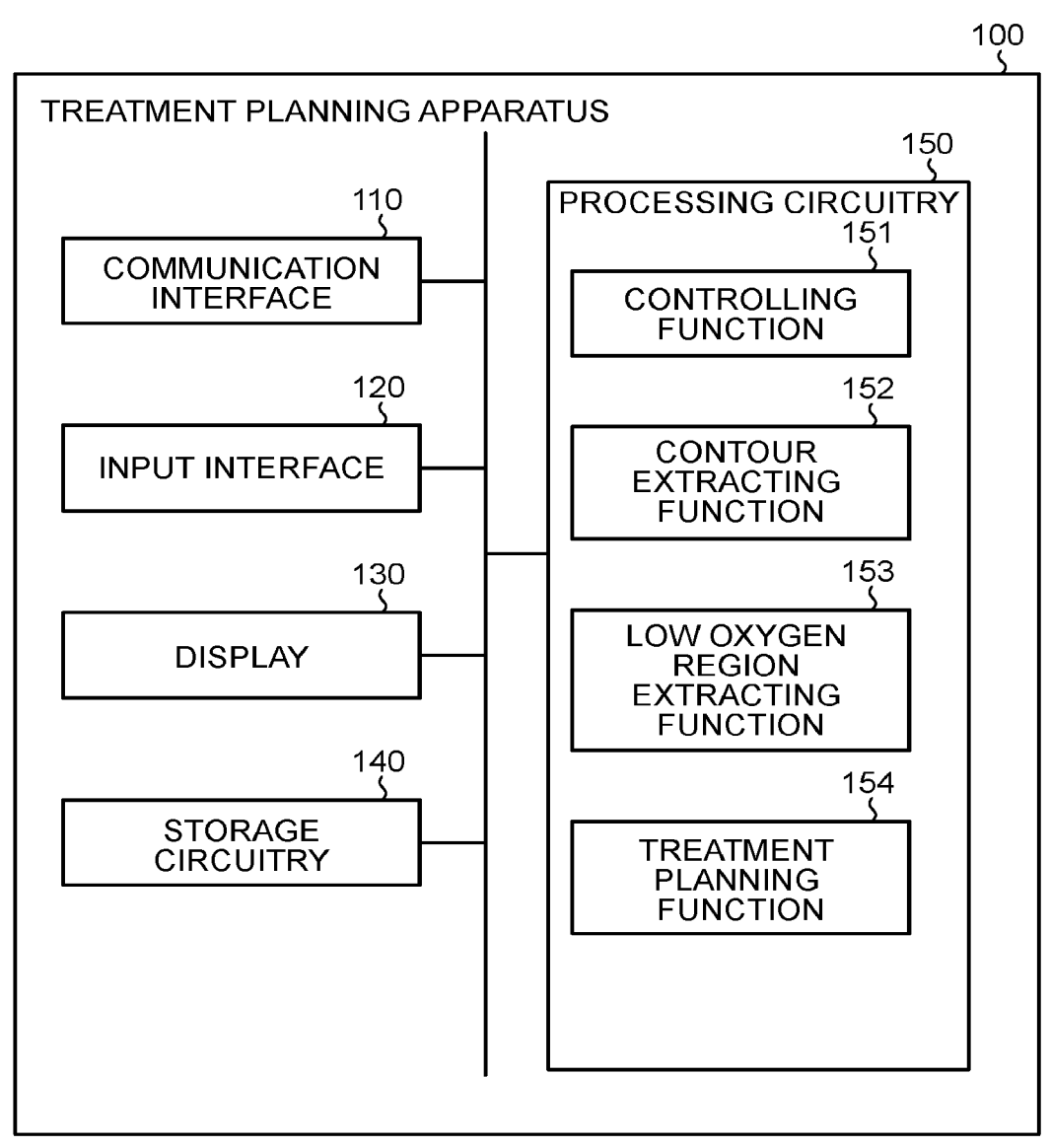
FIG. 2 is a diagram illustrating an exemplary configuration of a treatment planning apparatus according to the first embodiment.

Next, details of the treatment planning apparatus 100 according to the present embodiment will be explained. FIG. 2 is a diagram illustrating an exemplary configuration of the treatment planning apparatus 100 according to the first embodiment. As illustrated in FIG. 2, the treatment planning apparatus 100 includes a communication interface 110, an input interface 120, a display 130, storage circuitry 140, and processing circuitry 150 and makes it possible to carry out the radiation treatment on a low oxygen region, while making use of the bystander effect where irradiating only a partial region inside a tumor with radiation exerts treatment effects as far as on tumor cells in the surroundings.

The communication interface 110 is configured to control transfer of various types of data and communication performed between the treatment planning apparatus 100 and other apparatuses connected via a network. More specifically, the communication interface 110 is connected to the processing circuitry 150 and is configured to transmit data received from the other apparatuses to the processing circuitry 150 and to transmit data transmitted from the processing circuitry 150 to any of the other apparatuses. For example, the communication interface 110 is realized by using a network card, a network adaptor, a Network Interface Controller (NIC), or the like.

The input interface 120 is configured to receive, from a user, input operations of various types of instructions and various types of information. More specifically, the input interface 120 is connected to the processing circuitry 150 and is configured to convert the input operations received from the user into electrical signals and to transmit the electrical signals to the processing circuitry 150. For example, the input interface 120 may be realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 120 does not necessarily need to include physical operation component parts such as the mouse, the keyboard, and/or the like. For instance, possible examples of the input interface 120 include electrical signal processing circuitry configured to receive an electrical signal corresponding to an input operation from an external input mechanism provided separately from the apparatus and to transmit the electrical signal to controlling circuitry.

The display 130 is configured to display various types of information and various types of data. More specifically, the display 130 is connected to the processing circuitry 150 and is configured to display the various types of information and the various types of data received from the processing circuitry 150. For example, the display 130 is realized by using a liquid crystal display, a Cathode Ray Tube (CRT) display, an Organic Electroluminescence (EL) display, a plasma display, a touch panel, or the like. In the present embodiment, for example, the display 130 is configured to display a dose volume distribution called a Dose Volume Histogram (DVH) of a low oxygen region in a tumor region, as well as a DVH of organs at risk, and the treatment plan including the irradiation parameters such as the irradiation angle of the radiation, the dose and the shape of the irradiated field with respect to each irradiation angle, and the number of times of the irradiation.

The storage circuitry 140 is configured to store therein various types of data and various types of programs. More specifically, the storage circuitry 140 is connected to the processing circuitry 150 and is configured to store therein data received from the processing circuitry 150 and to read and transmit any of stored data to the processing circuitry 150. For example, the storage circuitry 140 is realized by using a semiconductor memory element such as a Random Access memory (RAM) or a flash memory, or a hard disk, an optical disk, or the like.

The processing circuitry 150 is configured to control the entirety of the treatment planning apparatus 100. For example, the processing circuitry 150 is configured to perform various types of processes in accordance with the input operations received from the user via the input interface 120. For example, the processing circuitry 150 is configured to receive data transmitted from other apparatuses via the communication interface 110 and to store the received data into the storage circuitry 140. Further, for example, the processing circuitry 150 is configured to transmit data received from the storage circuitry 140 to any of the other apparatuses, by transmitting the data to the communication interface 110. Furthermore, for example, the processing circuitry 150 is configured to cause the display 130 to display any of the data received from the storage circuitry 140.

In the present embodiment, for example, as illustrated in FIG. 2, the processing circuitry 150 is configured to execute a controlling function 151, a contour extracting function 152, a low oxygen region extracting function 153, and a treatment planning function 154. In this situation, the controlling function 151 is an example of a controlling unit. The contour extracting function 152 is an example of a first extracting unit. The low oxygen region extracting function 153 is an example of a second extracting unit. The treatment planning function 154 is an example of a treatment planning unit.

The controlling function 151 is configured to control data transmission/reception performed via the communication interface. For example, the controlling function 151 is configured to obtain the three-dimensional medical image from the medical image diagnosis apparatus 200. Further, the controlling function 151 is configured to transmit the treatment plan made by the treatment planning function 154 to the radiation treatment information system 300 and to the radiation treatment apparatus 400. Further, the controlling function 151 is configured to control display of various types of data (e.g., various types of information related to the treatment plan) on the display 130.

The contour extracting function 152 is configured to extract the tumor region rendered in the three-dimensional medical image. Further, the contour extracting function 152 is configured to extract, from the three-dimensional medical image, the organs at risk which are normal organs having a relatively high sensitivity to radiation and which should avoid being irradiated with radiation.

The low oxygen region extracting function 153 is configured to extract the low oxygen region in the tumor region.

The treatment planning function 154 is configured to make the treatment plan for the tumor region, while using the low oxygen region as an index.

Figure 3:
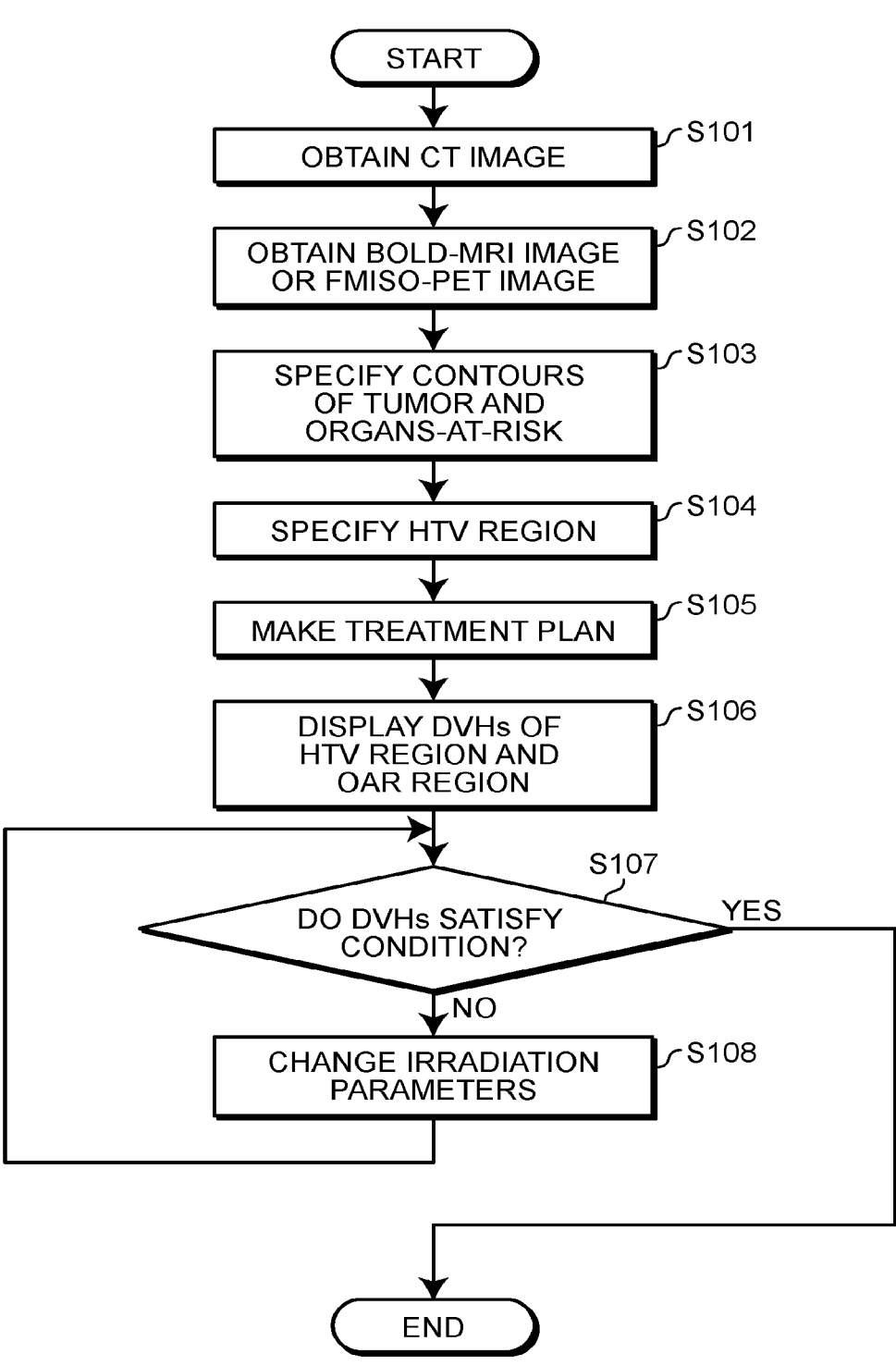
FIG. 3 is a flowchart illustrating a processing procedure of processes performed by the treatment planning apparatus according to the first embodiment.

Next, a procedure of processes performed by the treatment planning apparatus 100 will be explained with reference to FIG. 3, before details of each of the processes will be explained. FIG. 3 is a flowchart illustrating the processing procedure of the processes performed by the treatment planning apparatus 100 according to the first embodiment. In this situation, FIG. 3 illustrates an example in which a CT image is used as the three-dimensional medical image for making the treatment plan. Further, FIG. 3 illustrates the example in which, as a means for extracting the low oxygen region in the tumor region, a low oxygen region image (i.e., a Blood Oxygen Level Dependent (BOLD)-MRI image or a fluoromisonidazole (FMISO)-PET image) is used.

For example, as illustrated in FIG. 3, in the present embodiment, the controlling function 151 obtains the three-dimensional CT image of the treated subject from a CT apparatus for the treatment planning purpose (the medical image diagnosis apparatus 200) (step S101). In addition, the controlling function 151 either obtains the BOLD-MRI image of the treated subject from an MRI apparatus (the medical image diagnosis apparatus 200) or obtains the FMISO-PET image of the treated subject from a PET apparatus (the medical image diagnosis apparatus 200) (step S102). These processes are realized, for example, as a result of the processing circuitry 150 invoking and executing a program corresponding to the controlling function 151 from the storage circuitry 140.

Subsequently, the contour extracting function 152 specifies contours of the tumor and an organs-at-risk (OAR) region rendered in the three-dimensional CT image (step S103). This process is realized, for example, as a result of the processing circuitry 150 invoking and executing a program corresponding to the contour extracting function 152 from the storage circuitry 140.

After that, the low oxygen region extracting function 153 specifies a low oxygen region (hereinafter, a "Hypoxic Tumor Volume (HTV) region") in a tumor region (step S104). More specifically, the low oxygen region extracting function 153 specifies the HTV region in the tumor region specified by the contour extracting function 152. This process is realized, for example, as a result of the processing circuitry 150 invoking and executing a program corresponding to the low oxygen region extracting function 153 from the storage circuitry 140.

Subsequently, while using the HTV region as an index, the treatment planning function 154 makes the treatment plan for the tumor region (step S105). More specifically, on the basis of a radiation dose for the HTV region and a radiation dose for the OAR region, the treatment planning function 154 makes the treatment plan for the tumor region. This process is realized, for example, as a result of the processing circuitry 150 invoking and executing a program corresponding to the treatment planning function 154 from the storage circuitry 140.

After that, the controlling function 151 causes the display 130 to display the DVHs of the HTV region and the OAR region (step S106). This process is realized, for example, as a result of the processing circuitry 150 invoking and executing the program corresponding to the controlling function 151 from the storage circuitry 140.

Subsequently, the treatment planning function 154 judges whether or not the DVHs satisfy a condition (step S107). More specifically, the treatment planning function 154 judges whether or not the operator has approved the DVHs of the HTV region and the OAR region displayed on the display 130.

In this situation, when the DVHs do not satisfy the condition (step S107: No), the irradiation parameters included in the treatment plan are changed either manually by the operator or automatically by the treatment planning function 154 (step S108), and it is judged again whether or not the DVHs satisfy the condition (step S107). The processes at steps S107 and S108 are realized, for example, as a result of the processing circuitry 150 invoking and executing the program corresponding to the treatment planning function 154 from the storage circuitry 140.

On the contrary, when the DVHs satisfy the condition (step S107: Yes), the treatment planning function 154 ends the treatment plan making process. When the treatment plan making process has ended, the controlling function 151 transmits the treatment plan to the radiation treatment information system 300 and to the radiation treatment apparatus 400.

Next, details of each of the processes performed by the treatment planning apparatus 100 will be explained.
The Medical Image Obtaining Process As explained at steps S101 and S102 in FIG. 3, the controlling function 151 is configured to obtain the three-dimensional medical image obtained from the treated subject, in accordance with the medical image obtaining operation performed via the input interface 120. For example, the controlling function 151 is configured to obtain the three-dimensional CT image necessary for making the treatment plan for the treated subject. In this situation, when the CT image for the treatment planning purpose is taken, a fixture may be created to enhance reproducibility and holdability of the posture of the treated subject. Further, the treated subject may have, on the body surface thereof, a mark necessary for a position alignment so that the radiation is accurately applied in each session of the radiation treatment.

Figure 4A:
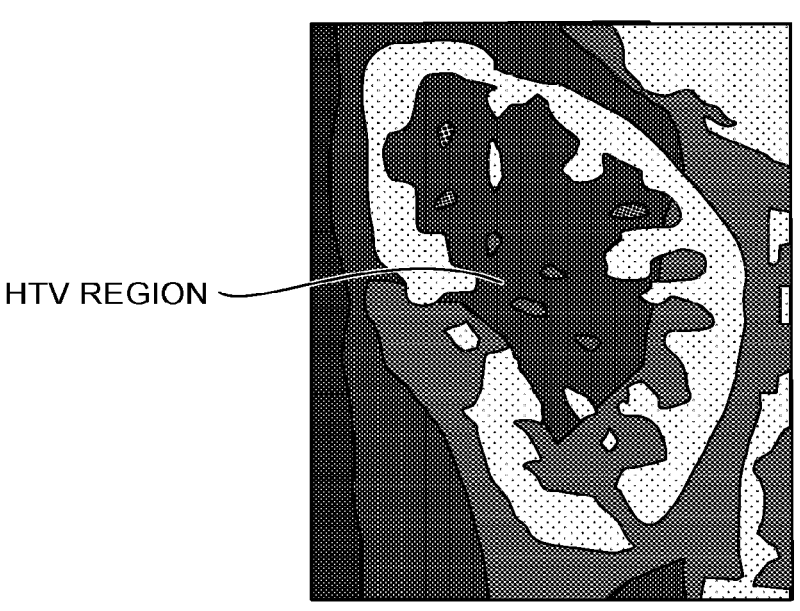
FIG. 4A is a drawing illustrating an example of a medical image for specifying a Hypoxic Tumor Volume (HTV) region according to the first embodiment.
Figure 4B:
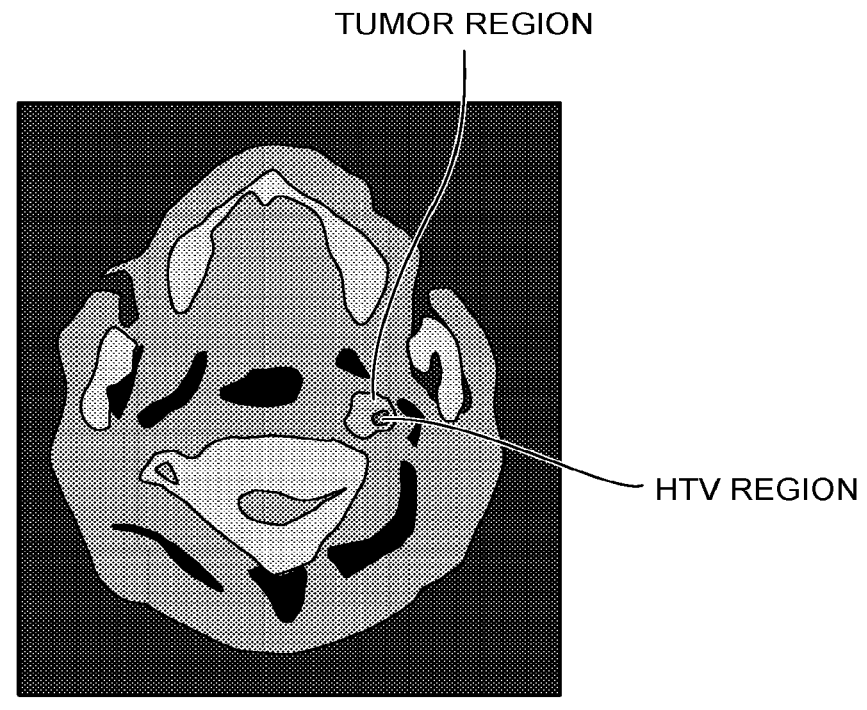
FIG. 4B is a drawing illustrating another example of the medical image for specifying the HTV region according to the first embodiment.

Further, the controlling function 151 is configured to obtain the medical image for specifying the HTV region in the tumor. FIGS. 4A and 4B are drawings illustrating examples of the medical image for specifying the HTV region according to the first embodiment. In the present example, FIG. 4A depicts a BOLD-MRI image, whereas FIG. 4B depicts an FMISO-PET image. Although FIGS. 4A and 4B depict the images two-dimensionally, the controlling function 151 is configured, in actuality, to obtain a three-dimensional BOLD-MRI image or a three-dimensional FMISO-PET image.

The BOLD-MRI image visualizes changes in an MR signal caused by differences in deoxyhemoglobin amounts within the blood. As illustrated in FIG. 4A, it is possible to discriminate an HTV region (a low oxygen region) from the other regions. Further, the FMISO-PET image visualizes an accumulated state of FMISO. As illustrated in FIG. 4B, it is possible to discriminate a region in a low oxygen state (a HTV region) in the tumor.

The Contour Extracting Process on the Tumor and the Organs at Risk

As explained at step S103 in FIG. 3, the contour extracting function 152 is configured to extract the contours of the tumor and the organs at risk rendered in the CT image obtained by the controlling function 151. More specifically, the contour extracting function 152 is configured to extract the contours of the tumor and the organs at risk, on the basis of a contouring (contour extraction) process realized as a manual process performed by the operator (a medical doctor) or as an automatic process using an image processing technique.

For example, when the contouring process using the manual process is implemented, the medical doctor sets the organs at risk, as well as a macroscopic tumor volume called a Gross Tumor Volume (GTV) which is a three-dimensional region where development and the presence of the organs at risk and the tumor can visually be recognized, and a Clinical Target Volume (CTV) which includes a tumor region that cannot be visually recognized but is potential, while viewing the CT image. The contour extracting function 152 is configured to specify the contours set by the medical doctor as the organs at risk, the GTV, and the CTV in the CT image.

Further, for example, when the contouring process using the automatic process is implemented, the contour extracting function 152 is configured to extract the organs at risk, the GTV, and the CTV rendered in the CT image, by using an existing image processing technique or a trained model obtained through machine learning.

The HTV Region Extracting Process

As explained at step S104 of FIG. 3, the low oxygen region extracting function 153 is configured to specify the HTV region within the tumor region in the CT image, on the basis of the low oxygen region image (the BOLD-MRI image or the FMISO-PET image) and the CT image. More specifically, to begin with, the low oxygen region extracting function 153 is configured to carry out a position alignment between the low oxygen region image and the CT image. Further, the low oxygen region extracting function 153 is configured to specify the HTV region in the CT image, on the basis of coordinates of the HTV in the low oxygen region image and coordinates of the tumor region in the CT image.

For example, the low oxygen region extracting function 153 is configured to calculate a correspondence relationship between the voxels in the low oxygen region image and voxels in the CT image, by using an existing linear position alignment algorithm, a non-linear position alignment algorithm, or a combination of these two algorithms. Further, the low oxygen region extracting function 153 is configured to specify the low oxygen region (the HTV region) of the tumor extracted from the CT image, on the basis of the calculated correspondence relationship.

The Treatment Plan Making Process

As explained at step S105 of FIG. 3, the treatment planning function 154 is configured to make the treatment plan for the tumor region specified from the CT image, while using the HTV region specified by the low oxygen region extracting function 153 as an index. More specifically, the treatment planning function 154 is configured to make the treatment plan including the irradiation parameters such as a region to be irradiated with the radiation (hereinafter, "radiation irradiation region"), an irradiation angle of the radiation, a dose and the shape of an irradiated field with respect to each irradiation angle, and the number of times of the irradiation.

Figure 5:
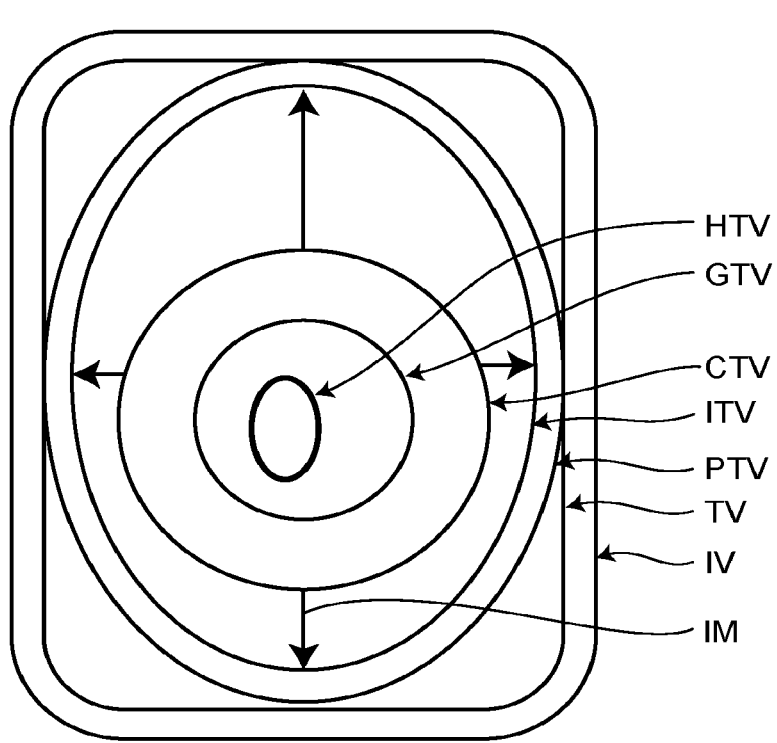
FIG. 5 is a drawing for explaining an irradiation region setting process according to the first embodiment.

Next, at first, a general process of setting a radiation irradiation region will be explained, with reference to FIG. 5. FIG. 5 is a drawing for explaining the irradiation region setting process according to the first embodiment. The process of setting the radiation irradiation region in radiation treatment is usually carried out by using the CTV set on the basis of the GTV described above. As explained above, the CTV is the region including the GTV and the tumor region that cannot visually be recognized but is potential. In an ordinary irradiation region setting process, as illustrated in FIG. 5, an Internal Target Volume (ITV) is set by adding, to the CTV, an Internal Margin (IM) for absorbing impacts from the movements of internal organs such as respiration, swallowing, cardiac pulsation, peristalsis, and/or the like.

Further, a Planning Target Volume (PTV) is set so as to include a Set-up Margin (SM) for each session of irradiation, and thus, the radiation irradiation region has been determined. In this situation, the Treatment Volume (TV) illustrated in FIG. 5 denotes a volume which is enclosed by an isodose curve and is determined to be the most appropriate for achieving a purpose of the treatment. The Irradiated Volume (IV) denotes a volume to be irradiated with a dose that is considered to be significant for tolerance of normal tissues.

In contrast, the treatment planning function 154 according to the present embodiment is configured to set the radiation irradiation region, while using the HTV region as an index. More specifically, the treatment planning function 154 is configured to determine the radiation irradiation region, by setting an ITV by adding an IM to the HTV region and further setting a PTV so as to include an SM. In this situation, the PTV set while using the HTV region as an index is smaller than the PTV illustrated in FIG. 5.

When the radiation irradiation region has been determined in this manner, the treatment planning function 154 is configured to set radiation irradiation conditions for the determined irradiation region. For example, the treatment planning function 154 is configured to set the irradiation conditions such as an irradiation angle of the radiation, a dose and the shape of an irradiated field with respect to each irradiation angle, and the number of times of the irradiation. In this situation, the shapes of the irradiated fields are formed, for example, by a Multi-Leaf Collimator (MLC) serving as a radiation limiter. The MLC includes a plurality of radiation blocking plates configured to set a radiation irradiation range and is capable of forming the irradiated field conforming to the shape of the radiation irradiation region, as a result of each of the blocking plates being independently driven on the basis of the treatment plan.

Figure 6A:
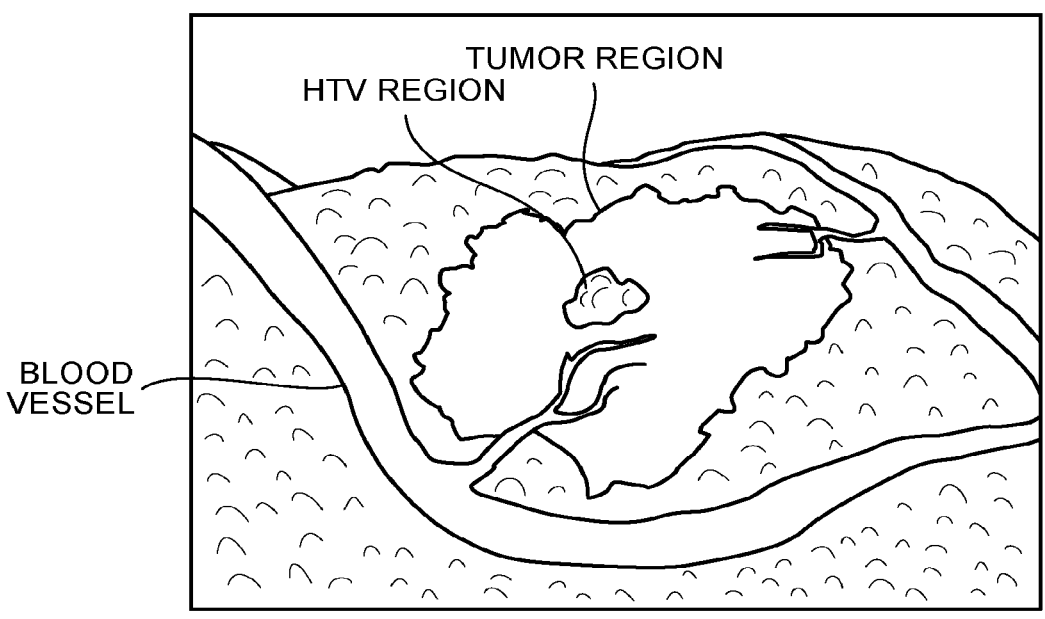
FIG. 6A is a drawing for explaining a bystander effect according to the first embodiment.
Figure 6B:
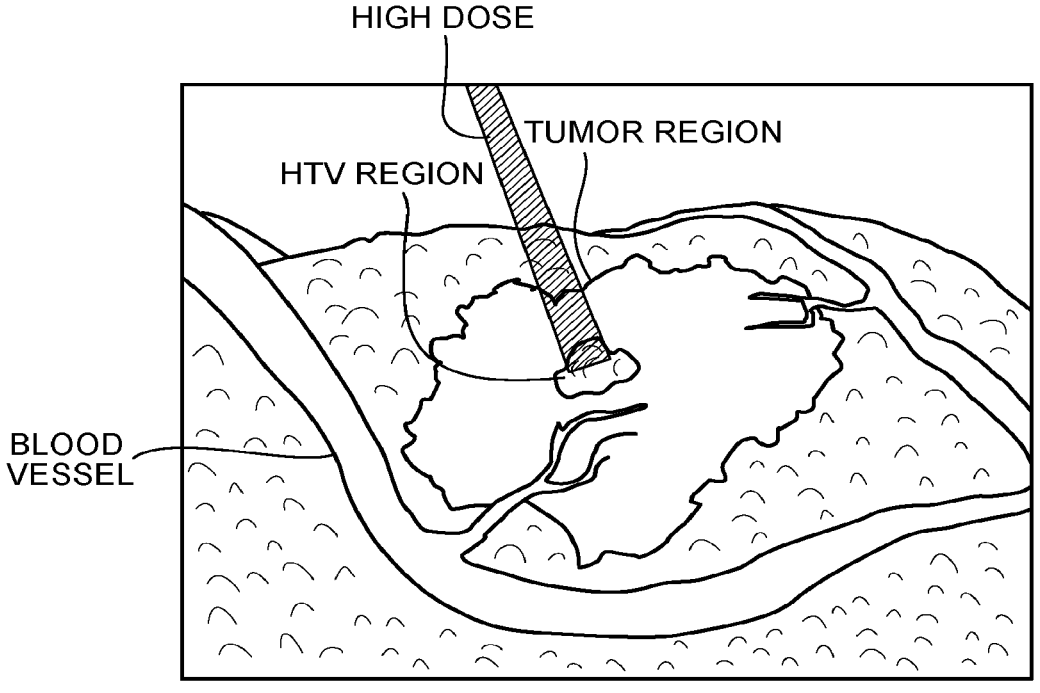
FIG. 6B is another drawing for explaining the bystander effect according to the first embodiment.

In this situation, the treatment planning function 154 is capable of setting the irradiation conditions taking the bystander effect into consideration. FIGS. 6A to 6E are drawings for explaining the bystander effect according to the first embodiment. As illustrated in FIG. 6A, when the tumor region includes an HTV region, the treatment planning function 154 is configured, as illustrated in FIG. 6B, to set the irradiation conditions so that the HTV region is irradiated with a high dose of radiation (a radiation dose sufficient for extinguishing the tumor cells in the HTV region).

Figure 6C:
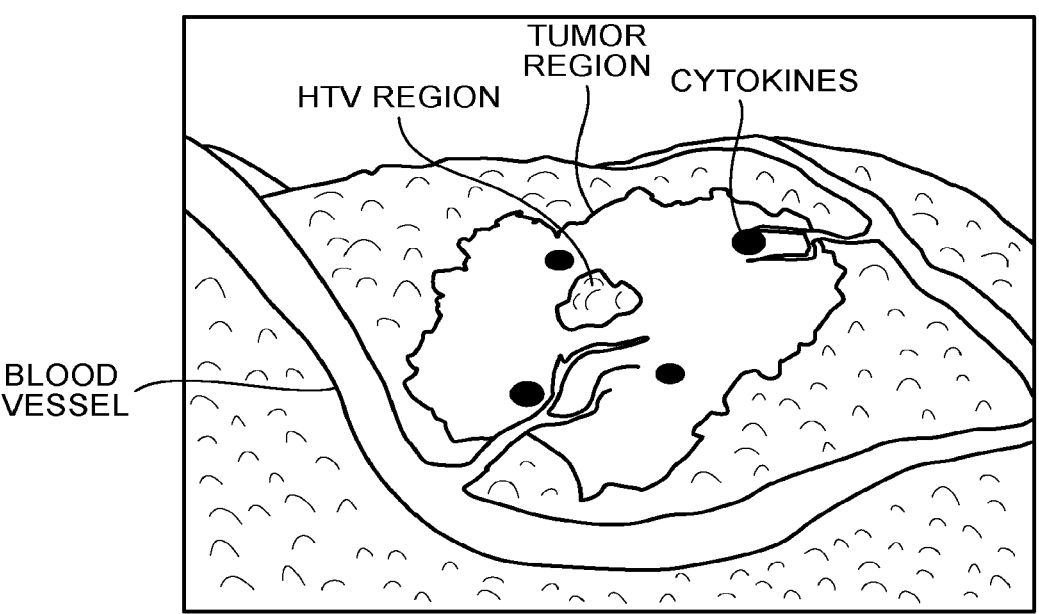
FIG. 6C is yet another drawing for explaining the bystander effect according to the first embodiment.
Figure 6D:
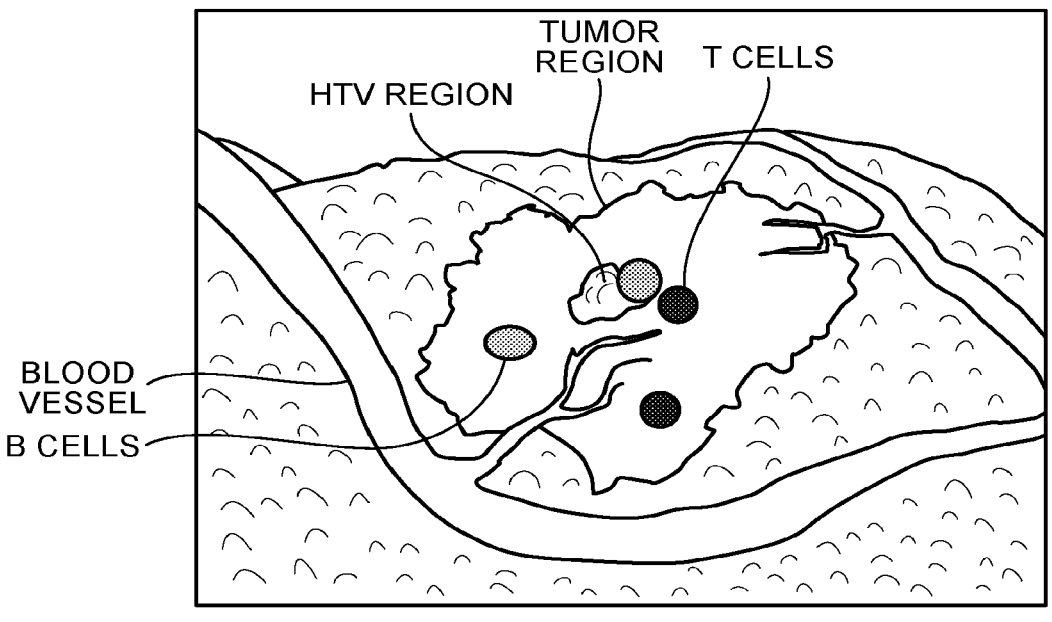
FIG. 6D is yet another drawing for explaining the bystander effect according to the first embodiment.
Figure 6E:
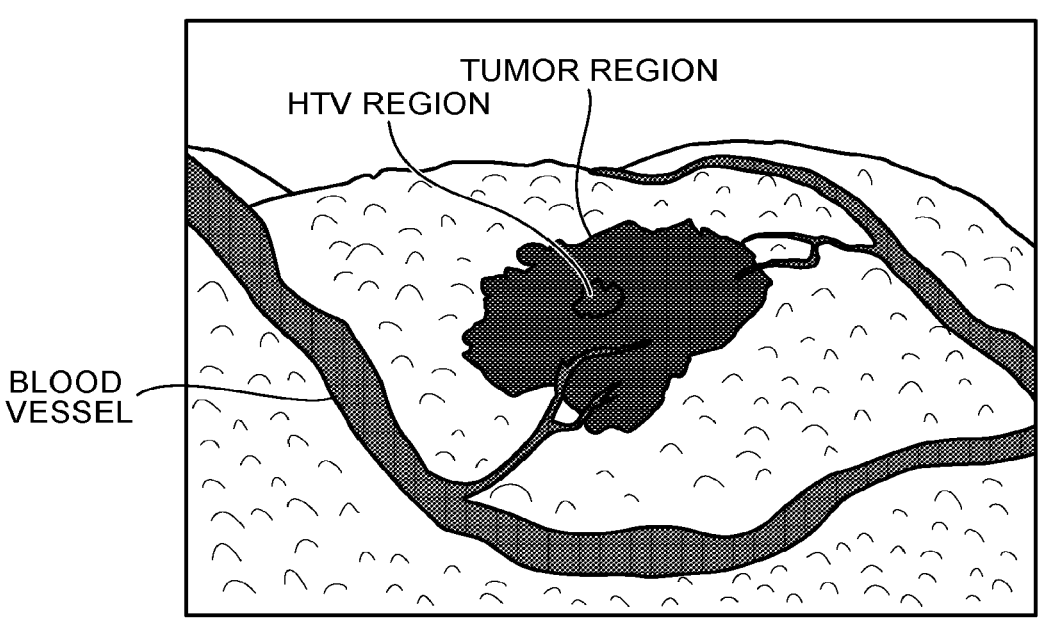
FIG. 6E is yet another drawing for explaining the bystander effect according to the first embodiment.

When the HTV region has been irradiated with the high dose of radiation described above, because cytokines are released, a tumor control action due to immunity occurs in the tumor cells in the surroundings of the HTV region (the cells that have not been irradiated) (FIG. 6C). In addition, a tumor control action is also exerted by B cells and T cells on the tumor cells in the surroundings (FIG. 6D). As a result of these bystander effects, it is possible to extinguish the entire tumor including the HTV region irradiated with the radiation and the surrounding region (FIG. 6E).

As explained above, as a result of the treatment planning function 154 establishing the setting during the irradiation condition setting process, so that only the HTV region is irradiated with the high dose of radiation, it is possible to extinguish the tumor cells in the HTV region having radiation resistance with the radiation and to also extinguish the tumor cells in the other regions by using the bystander effect. It is therefore possible to have a treatment plan capable of reducing side effects, while enhancing the effects of the treatment.

In this situation, the radiation dose with which the HTV region is irradiated may be set as a high dose that is fatal for the tumor cells in the HTV region or may be set as a dose based on the assumption that a boost irradiation or a sensitizer will be used. In other words, the treatment planning function 154 is configured to set the irradiation conditions with a dose targeting the tumor cells in the HTV region.

As explained above, the treatment planning function 154 is configured to set the irradiation parameters such as the radiation irradiation region, the irradiation angle of the radiation, the dose and the shape of the irradiated field with respect to each irradiation angle, and the number of times of the irradiation and is configured, on the condition that the set parameters are approved by the operator (the medical doctor), to determine the set parameters as a treatment plan.

The DVH Display Process

Figure 7:
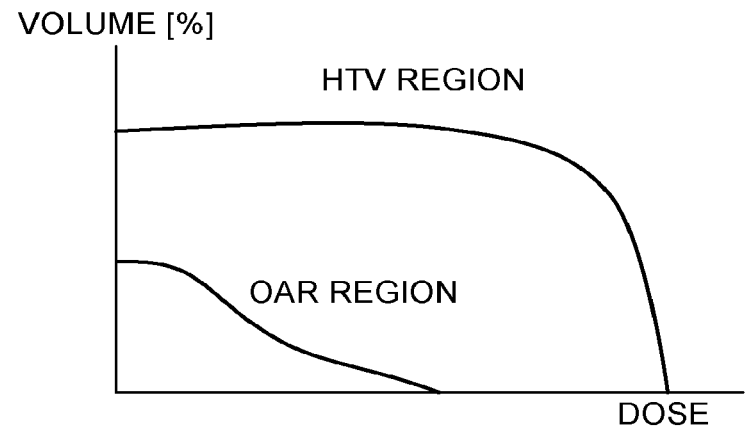
FIG. 7 is a chart illustrating an example of Dose Volume Histograms (DVHs) according to the first embodiment.

As explained at step S107 in FIG. 3, the controlling function 151 is configured to cause the display 130 to display the DVH of the HTV region and the DVH of the OAR region with respect to each of the irradiation parameters set by the treatment planning function 154. FIG. 7 is a chart illustrating an example of the DVHs according to the first embodiment. In the present example, while the vertical axis expresses the volume (%), whereas the horizontal axis expresses the dose, the DVHs in FIG. 7 indicate, in a graph, relationships between doses and volumes in the HTV region and the OAR region of which the contours were specified. In other words, the DVHs in FIG. 7 indicate results of dose calculations with respect to each of the three-dimensional regions specified in the CT image.

For example, the controlling function 151 is configured to cause a DVH, such as those illustrated in FIG. 7, to be displayed with respect to each of the irradiation parameters. The operator (the medical doctor) refers to the DVHs such as those illustrated in FIG. 7 and selects irradiation parameters so that as large a volume as possible (closer to 100%) is irradiated with a high dose of radiation regarding the curve indicating the DVH of the HTV region and so that as small a volume as possible (closer to 0%) is irradiated with a high dose of radiation regarding the curve indicating the DVH of the OAR region. That is to say, the treatment planning function 154 is configured to perform a simulation under various irradiation conditions, while varying the irradiation parameters such as the radiation irradiation direction and the dose of the irradiation, according to operations of the operator. In other words, the treatment planning function 154 is configured to make a treatment plan corresponding to the radiation irradiation parameters determined on the basis of the DVH of the HTV region and the DVH of the OAR region. The controlling function 151 is configured to cause the display 130 to display the DVHs corresponding to the varied irradiation parameters.

As explained above, the operator optimizes the treatment plan, by selecting an optimal beam path that makes the DVH of the HTV region high and makes the DVH of the OAR region low. The treatment planning function 154 is configured to determine the treatment plan approved (optimized) by the operator, as the treatment plan for the tumor specified in the CT image.

The treatment plan made in this manner is transmitted to the radiation treatment information system 300, so as to be managed together with patient information, a treatment history, and the like.

At the Time of the Radiation Treatment

At the time of the radiation treatment, the treatment plan is transmitted from the radiation treatment information system 300 to the radiation treatment apparatus 400. The radiation treatment apparatus 400 is configured to irradiate the treated subject lying on the tabletop with the radiation, according to the received treatment plan.

For example, the radiation treatment apparatus 400 includes a gantry having a console, a radiation generator, a radiation limiter (the MLC), and an imaging apparatus (an X-ray generator and an X-ray detector), and a table apparatus having a tabletop and is configured to carry out the radiation treatment on the basis of control exercised by the console. More specifically, a processing function of processing circuitry included in the console is configured to carry out the radiation treatment, by controlling the gantry and the table apparatus on the basis of the treatment plan made by the treatment planning apparatus 100. For example, the processing function is configured to obtain the treatment plan from the treatment planning apparatus 100 via the radiation treatment information system 300. Further, the processing function is configured to irradiate the treated subject lying on the tabletop with the radiation, by setting the gantry at the irradiation angle according to the treatment plan by rotating the gantry. In this situation, the processing function is an example of a processing unit.

As explained above, according to the first embodiment, the contour extracting function 152 is configured to extract the tumor region rendered in the medical image. The low oxygen region extracting function 153 is configured to extract the low oxygen region in the tumor region. The treatment planning function 154 is configured to make the treatment plan for the tumor region, by using the low oxygen region as the index. Consequently, the treatment planning apparatus 100 according to the first embodiment is capable of carrying out the treatment on the low oxygen region by using the radiation while setting the radiation irradiation parameters for the low oxygen region and also treating the surrounding region by using the bystander effect and thus makes it possible to carry out the radiation treatment making use of the bystander effect.

Further, according to the first embodiment, the treatment planning function 154 is configured to make the treatment plan for the tumor region, on the basis of the radiation dose for the low oxygen region (the HTV region) and the radiation dose for the organs at risk (the OAR region), which are normal organs having a relatively high sensitivity to radiation. Consequently, the treatment planning apparatus 100 according to the first embodiment makes it possible to appropriately irradiate the HTV region with the radiation.

Further, according to the first embodiment, the controlling function 151 is configured to cause the display 130 to display the dose volume distribution (the DVH) of the low oxygen region (the HTV region) and the dose volume distribution (the DVH) of the organs at risk (the OAR region), with respect to each of the radiation irradiation parameters. The treatment planning function 154 is configured to make the treatment plan corresponding to the one set of radiation irradiation parameters determined on the basis of the dose volume distribution in the low oxygen region and the dose volume distribution in the organs at risk. Consequently, the treatment planning apparatus 100 according to the first embodiment makes it possible to make the appropriate treatment plan for the HTV region.

First Modification Example

In the above embodiment, the example was explained in which only the radiation for the HTV region is addressed. However, possible embodiments are not limited to this example. For instance, it is also acceptable to make a treatment plan taking the GTV into consideration. In that situation, the treatment planning function 154 is configured to make the treatment plan including the radiation irradiation based on the tumor region (the GTV region), in addition to the radiation irradiation based on the low oxygen region (the HTV region).

In other words, the treatment planning function 154 is configured to make the treatment plan so as to further irradiate the GTV with the radiation, in addition to the radiation irradiation based on the HTV region described in the first embodiment. For example, the treatment planning function 154 is configured to make the treatment plan so as to irradiate a region (e.g., a region obtained by reducing the contour of the GTV by a margin of a number of millimeters) having a smaller contour than the contour of the GTV, with radiation having a lower dose than normal. As a result, on the tumor cells other than those in the low oxygen region, it is possible to exert a treatment effect from the bystander effect and a treatment effect from the radiation, and it is therefore possible to achieve higher effects. Further, by irradiating the region having the contour smaller than the contour of the GTV with the lower dose of radiation, it is also possible to reduce impacts on normal cells in the periphery of the tumor.

As explained above, according to the first modification example, the treatment planning function 154 is configured to make the treatment plan including the radiation irradiation based on the tumor region, in addition to the radiation irradiation based on the low oxygen region. Consequently, in the radiation treatment making use of the bystander effect, the treatment planning apparatus 100 according to the first modification example makes it possible to carry out the treatment having the higher effect, while suppressing the impacts on the normal cells in the periphery of the tumor.

Second Modification Example

In the embodiment described above, the example was explained in which the treatment plan is made once for the radiation treatment. However, possible embodiments are not limited to this example. It is also acceptable to carry out an Adaptive Radiation Therapy (ART) in which treatment plans are corrected as the treatment progresses. In that situation, for example, a low oxygen region image may be acquired regularly, so as to carry out the ART by using the acquired low oxygen region images.

Further, for example, when the radiation treatment apparatus 400 is an MR-Linac system, the radiation treatment apparatus 400 may be configured to acquire a BOLD-MRI image before the treatment and to transmit the acquired BOLD-MRI image to the treatment planning apparatus 100. By correcting the treatment plan on the basis of the received BOLD-MRI image, the treatment planning apparatus 100 makes it possible to easily carry out appropriate radiation treatment suitable for the progress of the treatment.

Second Embodiment

In a second embodiment, an example will be explained in which treatment plans are switched in accordance with the size of the HTV region. For example, some tumors may have a small HTV region, and irradiating such a small region with radiation may not exert the bystander effect in some situations. To cope with these situations, the treatment planning apparatus 100 according to the second embodiment is configured to switch between a treatment plan based on the HTV region and a treatment plan based on the GTV, depending on the size of the HTV region. In this situation, the treatment planning apparatus 100 according to the second embodiment is different from that of the first embodiment for processes performed by the treatment planning function 154. Thus, the differences will primarily be explained below.

When the ratio of the volume of the HTV region to the volume GTV is smaller than a threshold value, the treatment planning function 154 according to the second embodiment is configured to make a treatment plan for the GTV on the basis of a radiation dose for the GTV and a radiation dose for the organs at risk (the OAR region), which are normal organs having a relatively high sensitivity to radiation. In other words, when the volume of the HTV region is small, the treatment planning function 154 is configured to make a normal treatment plan based on the GTV. On the contrary, when the ratio of the volume of the HTV region to the volume GTV is equal to or larger than the threshold value, the treatment planning function 154 is configured to make the treatment plan described in the first embodiment. In this situation, the threshold value used for determining the ratio of the volume of the HTV region to the volume GTV may arbitrarily be set.

When the normal treatment plan based on the GTV is made, the controlling function 151 according to the second embodiment is capable of causing the display 130 to display a DVH of the GTV and a DVH of the OAR region.

As explained above, according to the second embodiment, when the ratio of the volume of the HTV region to the volume GTV is smaller than the threshold value, the treatment planning function 154 is configured to make the treatment plan for the GTV, on the basis of the radiation dose for the GTV and the radiation dose for the OAR region. Consequently, the treatment planning apparatus 100 according to the second embodiment makes it possible to make an appropriate treatment plan in accordance with the size of the HTV region.

Other Embodiments

The first and the second embodiments have thus been explained. It is also possible to carry out the present disclosure in various different modes, other than the first and the second embodiments described above.

In the above embodiments, the example was explained in which the BOLD-MRI image or the FMISO-PET image is used as a means for specifying the low oxygen region in the tumor; however, possible embodiments are not limited to this example. It is also acceptable to use any means, as long as the means is capable of specifying the low oxygen region in the tumor.

In the above embodiments, the processing functions included in the processing circuitry 150 were explained. In this regard, for example, the abovementioned processing functions are stored in the storage circuitry 140 in the form of computer-executable programs. The processing circuitry 150 is configured to realize the processing functions corresponding to the programs, by reading the programs from the storage circuitry 140 and executing the read programs. In other words, the processing circuitry 150 that has read the programs have the processing functions illustrated in FIG. 2.

Although the example was explained with reference to FIG. 2 in which the processing functions are realized by the single piece of processing circuitry (i.e., the processing circuitry 150), possible embodiments are not limited to this example. For instance, it is also acceptable to structure the processing circuitry 150 by combining together a plurality of independent processors, so that the processing functions are realized as a result of the processors executing the programs. Further, the processing functions included in the processing circuitry 150 may be realized as being distributed among or integrated into one or more pieces of processing circuitry, as appropriate.

Further, the term "processor" used in the description of the above embodiments denotes, for example, a Central Processing Unit (CPU), a Graphics Processing Unit (GPU), or circuitry such as an Application Specific Integrated Circuit (ASIC) or a programmable logic device (e.g., a Simple Programmable Logic Device (SPLD), a Complex Programmable Logic Device (CPLD), or a Field Programmable Gate Array (FPGA)). In this situation, instead of having the programs saved in the storage circuitry, it is also acceptable to directly incorporate the programs in the circuitry of one or more processors. In that situation, the one or more processors realize the functions by reading and executing the programs incorporated in the circuitry thereof. Further, the processors in the present embodiments do not each necessarily have to be structured as a single piece of circuitry. It is also acceptable to structure one processor by combining together a plurality of pieces of independent circuitry so as to realize the functions thereof.

In this situation, the programs executed by the processors are provided as being incorporated, in advance, in a Read Only Memory (ROM), a storage unit, or the like. Alternatively, the programs may be provided as being stored in a computer-readable storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable by those apparatuses. Further, the programs may be stored in a computer connected to a network such as the Internet so as to be provided or distributed as being downloaded via the network. For example, the programs are structured with modules including functional units. In the actual hardware, as a result of a CPU reading and executing the programs from a storage medium such as the ROM, the modules are loaded into a main storage apparatus and generated in the main storage apparatus.

According to at least one aspect of the embodiments described above, it is possible to carry out the radiation treatment making use of the bystander effect.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A treatment planning apparatus, comprising:
processing circuitry configured to
extract a tumor region rendered in a medical image;
extract a low-oxygen region in the tumor region; and
set a Planning Target Volume (PTV) for the extracted tumor region containing the low-oxygen region, the PTV being smaller than a PTV for a tumor region without a low-oxygen region.

2. The treatment planning apparatus according to claim 1, wherein the processing circuitry is further configured to make a treatment plan for the tumor region, based on a radiation dose for the low-oxygen region and a radiation dose for an organ at risk, which is a normal organ having a relatively high sensitivity to radiation.

3. The treatment planning apparatus according to claim 2, wherein the processing circuitry is further configured to;
cause a display to display a dose volume distribution in the low-oxygen region and a dose volume distribution in the organ at risk, with respect to each of radiation irradiation parameters, and
make the treatment plan in accordance with one of the radiation irradiation parameters determined based on the dose volume distribution in the low-oxygen region and the dose volume distribution in the organ at risk.

4. The treatment planning apparatus according to claim 1, wherein the processing circuitry is further configured to make the treatment plan including a radiation irradiation based on the tumor region, in addition to a radiation irradiation based on the low-oxygen region.

5. The treatment planning apparatus according to claim 1, wherein, when a ratio of a volume of the low-oxygen region to a volume of the tumor region is smaller than a threshold value, the processing circuitry is further configured to make the treatment plan for the tumor region, based on a radiation dose for the tumor region and a radiation dose for an organ at risk, which is a normal organ having a relatively high sensitivity to radiation.

6. A radiation treatment apparatus, comprising:
circuitry configured to
obtain the treatment plan made by the treatment planning apparatus according to claim 1; and
perform radiation treatment based on the obtained treatment plan.

7. A treatment planning method, comprising:
extracting a tumor region rendered in a medical image;
extracting a low-oxygen region in the tumor region; and
setting a Planning Target Value (PTV) for the tumor region containing the low-oxygen region, the PTV being smaller than a PTV for a tumor region without a low-oxygen region.

* * * * *